United States Patent
Lee

(10) Patent No.: US 6,180,418 B1
(45) Date of Patent: Jan. 30, 2001

(54) FORCE DISCRIMINATION ASSAY

(75) Inventor: Gil U. Lee, Alexandria, VA (US)

(73) Assignee: The United States of America as represented by the Secretary of the Navy, Washington, DC (US)

(*) Notice: Under 35 U.S.C. 154(b), the term of this patent shall be extended for 0 days.

(21) Appl. No.: 09/008,782

(22) Filed: Jan. 20, 1998

(51) Int. Cl.$^7$ ............................ C12Q 1/68; G01N 33/553
(52) U.S. Cl. ............................ 436/526; 435/6; 436/526
(58) Field of Search ............................ 435/6; 436/526; 525/54.1

(56) References Cited

U.S. PATENT DOCUMENTS

| | | |
|---|---|---|
| 5,240,994 | 8/1993 | Brink et al. . |
| 5,318,914 | 6/1994 | Matte et al. . |
| 5,372,930 | 12/1994 | Colton et al. . |
| 5,445,971 | 8/1995 | Rohr . |
| 5,558,839 | 9/1996 | Matte et al. . |
| 5,580,923 * | 12/1996 | Yeung et al. ............ 525/54.1 |
| 5,605,662 | 2/1997 | Heller et al. . |
| 5,776,748 * | 7/1998 | Singhvi et al. ............ 435/180 |

OTHER PUBLICATIONS

Yamanski et al., "Fluctuation analysis of myosin–coated bead movement along actin bundels og Nitella" vol. 221, pp. 831–836, 1996.*

Kai–Chien et al., Influence of Direction and Type of Applied Force on the Detachment of Macromolecularly–Bound Particles from Surfaces, Langmuir 1996, 12, 2271–2282.

* cited by examiner

Primary Examiner—John S. Brusca
Assistant Examiner—Jeffrey S. Lundgren
(74) Attorney, Agent, or Firm—John J. Karasek

(57) ABSTRACT

A sensor for a selected target species has (a) a substrate which has been chemically modified by attachment of substrate modifiers; (b) one or more magnetically active beads which have been chemically modified by attachment of bead modifiers, where these bead modifiers will have a binding affinity for the substrate modifiers in the presence of the target species, and a measurably different binding affinity for the substrate modifiers in the absence of the target species; (c) an adjustable source of a magnetic field for exerting a force on the beads; and (d) an imaging system, for observing and counting beads bound to the substrate. In a preferred embodiment, the invention further has a system for identifying clusters of beads, and for removing the effect of such clusters from measurements of the target analyte. As with other assays, the sensor relies on the ability of certain molecules to bind with specific target (analyte) molecules. By coating the beads and the substrate with appropriate molecules, the beads will (or will not) bind specifically to the substrate in the presence (or absence) of the target molecule. When a magnetic field is applied to the substrate, the magnetic beads will be pulled away from the substrate. If the beads are specifically bound to the substrate, however, the beads will be retained on the substrate, indicating the presence (or absence) of the target species.

23 Claims, 6 Drawing Sheets

FORCE DISCRIMINATION ASSAY

BACKGROUND OF THE INVENTION

1. Field of the Invention

The present invention relates generally to assays and more specifically to binding assays, such as antibody/hapten or DNA interactions, taking advantage of the differing strengths of these interactions from each other and from non-specific binding interactions, and using labels that respond to a magnetic field.

2. Description of the Related Art

Binding assays, for example immunoassays, are widely used in the food, medical, and pharmaceutical industries as diagnostic tests for a wide range of target molecules. Many binding assays have been produced and marketed since the principle was first developed.

Immunoassays typically exploit the binding capabilities of antibodies. Antibodies are protein molecules which are frequently considered fighters of infections. They fight infections by binding to the infectious material in a specific manner, forming a complex. This is a signal to the organism to reject that complex. Antibodies may also be produced to specifically bind to a wide range of compounds, as a key fits a lock. However other molecules (e.g., chelators, strands of polynucleic acids, receptors including cellular receptors) that are capable of recognizing and selectively binding other molecules may be employed to detect a wide range of species, such as polynucleic acids (DNA or RNA), polypeptides, glycolipids, hormones, polymers, metal ions, and certain low molecular weight organic species including a number of illegal drugs. To be useful in an assay, this recognition event must generate a signal that is macroscopically observable. The method employed to generate such a signal is one way of distinguishing the various types of immunoassays.

In the initial embodiment of an immunoassay, radioactivity was employed. This radioimmunoassay (RIA) is quite sensitive and widely used, but the hazards, expense, and restrictions associated with handling radioactive material makes alternative immunoassays desirable. Recently, enzyme and fluorescence assays have replaced radioassays.

A few immunoassays use magnetically active labels to detect chemical compounds, and associate the force applied by these magnetic labels in a magnetic field with the amount of the analyte present. See U.S. Pat. Nos. 5,445,970 and 5,445,971, both issued on Aug. 29, 1995 to Rohr.

The Rohr patents use magnetically active beads, an externally applied magnetic field, and a balance for monitoring the force applied by these beads to a chemically modified substrate. In a typical embodiment (a sandwich assay), both the magnetically active beads and the substrate are modified to have antibodies for the analyte bound to their surfaces. The antibody—antibody interactions between the beads and the substrate will not produce specific binding interactions, although some non-specific adsorption may occur. If an external magnetic field is applied, the field will separate the beads from the substrate. If the analyte is introduced into the system, it will bind to the beads and the substrate in a sandwich configuration, thus linking the beads to the substrate through a specific binding interaction. When an external magnetic field is applied to this system, the field will, depending on its orientation, push or pull on the beads, changing the force measured by the balance, thereby indicating the presence and (in principle) amount of analyte present.

One of the drawbacks of Rohr's work is that it only measures an integrated signal related to the behavior of a multitude of beads experiencing a range of magnetic conditions. This is particularly problematic, because the work of the present inventors has shown that the beads in this system interact in complex ways.

Referring to FIG. 1, a significant fraction of beads in Rohr's system will tend to clump together, and the behavior of these clumped beads is not easily modeled. FIG. 1 depicts typical paramagnetic beads on a substrate, in an applied magnetic field, as they might be seen through a typical optical microscope. One sees from FIG. 1 that some of the beads aggregate into strings and clusters. In some cases, the bead dipoles may align, creating a larger magnetic moment than anticipated. Rohr's invention takes into account none of this behavior, and thus is plagued by low sensitivity. A more reliable qualitative and quantitative system would monitor the behavior of individual beads, and correct for or cancel the effect of complex interactions that would be a source of errors in Rohr's system. Additionally, such a system would inherently be more precise, since each bead could be monitored.

A second drawback of Rohr's work is the unstated assumption that time is not a variable in this system. Each of the assays disclosed in Rohr's patents show the signal to be associated with only the concentration of the analyte. The work of the present inventors has shown that the magnetic beads in an applied field will dissociate from a substrate as a function of time and temperature, following a Boltzmann distribution curve.

An improved binding assay sensor would allow for the discrimination between complex binding interactions at the single bead level. An improved binding assay sensor would also provide additional information beyond the presence or absence of a binding interaction, such as information about the strength of that specific interaction. A part of developing such additional information, it would be valuable to have a method for developing force-binding curves for target analytes.

SUMMARY OF THE INVENTION

Accordingly, it is an object of this invention to selectively detect a wide range of target species, with a high degree of sensitivity.

It is a further object of this invention to detect target species using a transduction mechanism that is independent of the mass of the species.

It is a further object of this invention to obtain additional information beyond the presence or absence of a binding interaction, such as information about the strength of that specific interaction.

It is a further object of the invention to characterize the strength of specific binding interactions.

It is a further object of the invention to develop force-binding curves for a wide range of analyte species.

It is a further object of the invention to use magnetically active beads in an assay that can discriminate the activity of single beads.

It is a further object of the invention to use magnetically active beads in an assay that can isolate the effects of complex magnetic interactions between clusters of beads.

It is a further object of the invention to use magnetically active beads in an assay that can account for the effects of time and temperature on populations of beads bound to a substrate, i.e., the Boltzmann effect.

These and additional objects of the invention are accomplished by the structures and processes hereinafter described.

An aspect of the present invention is a sensor for a selected target species having (a) a substrate which has been chemically modified by attachment of substrate modifiers; (b) one or more magnetically active beads which have been chemically modified by attachment of bead modifiers, where these bead modifiers will have a binding affinity for the substrate modifiers in the presence of the target species, and a measurably different binding affinity for the substrate modifiers in the absence of the target species; (c) an adjustable source of a magnetic field for exerting a force on the beads; and (d) an imaging system, for observing and counting beads bound to said substrate.

In a preferred embodiment, the invention further has a system for identifying clusters of beads, and for removing the effect of such clusters from measurements of the target analyte.

Another aspect of the present invention is a method for sensing the presence of selected target species, having the steps of (a) modifying a substrate by attaching a substrate modifier; (b) modifying one or more magnetically active beads by attaching bead modifiers, where these bead modifiers have a binding affinity for the substrate modifiers in the presence of the target species, and a measurably different binding affinity for the substrate modifiers in the absence of the target species; (c) disposing the beads and/or the substrate in a solution suspected of containing the target molecule; (d) permitting the beads to interact with the substrate, where the interactions may include both specific and non-specific binding; (e) applying a uniform magnetic field to the sample area, preferably normally with respect to the substrate, for pulling the beads away from the substrate; and (f) observing the beads. In a preferred embodiment, this method also has the steps of counting beads observed to be bound to the substrate after, and preferably also before, the introduction of the solution suspected of containing the target analyte.

Another aspect of the present invention is a method for determining the strength of the interaction between a target species and a species that undergoes a specific binding interaction with that target species, having the steps of (a) modifying a substrate by attaching a substrate modifier; (b) modifying one or more magnetically active beads by attaching bead modifiers, where these bead modifiers have a binding affinity for the substrate modifiers in the presence of the target species, and a measurably different binding affinity for the substrate modifiers in the absence of the target species; (c) disposing the beads and the substrate in a solution containing the target molecule; (d) permitting the beads to interact with the substrate; (e) applying a uniform magnetic field to the sample area, preferably normally with respect to the substrate, for pulling the beads away from the substrate; (f) varying the strength of this magnetic field until beads separate from the substrate, and (g) observing the beads.

BRIEF DESCRIPTION OF THE DRAWINGS

A more complete appreciation of the invention will be obtained readily by reference to the following Description of the Preferred Embodiments and the accompanying drawings in which like numerals in different figures represent the same structures or elements, wherein.

DETAILED DESCRIPTION OF THE PREFERRED EMBODIMENTS

The present invention relies on identifying the force required to separate labeled beads from a substrate. To ensure a high sensitivity and consistent results, it is desired to keep the forces acting on the beads simple (i.e., readily analyzed) and uniform (i.e., essentially the same for all beads in a sample and reproducible from run-to-run).

Figure 1:
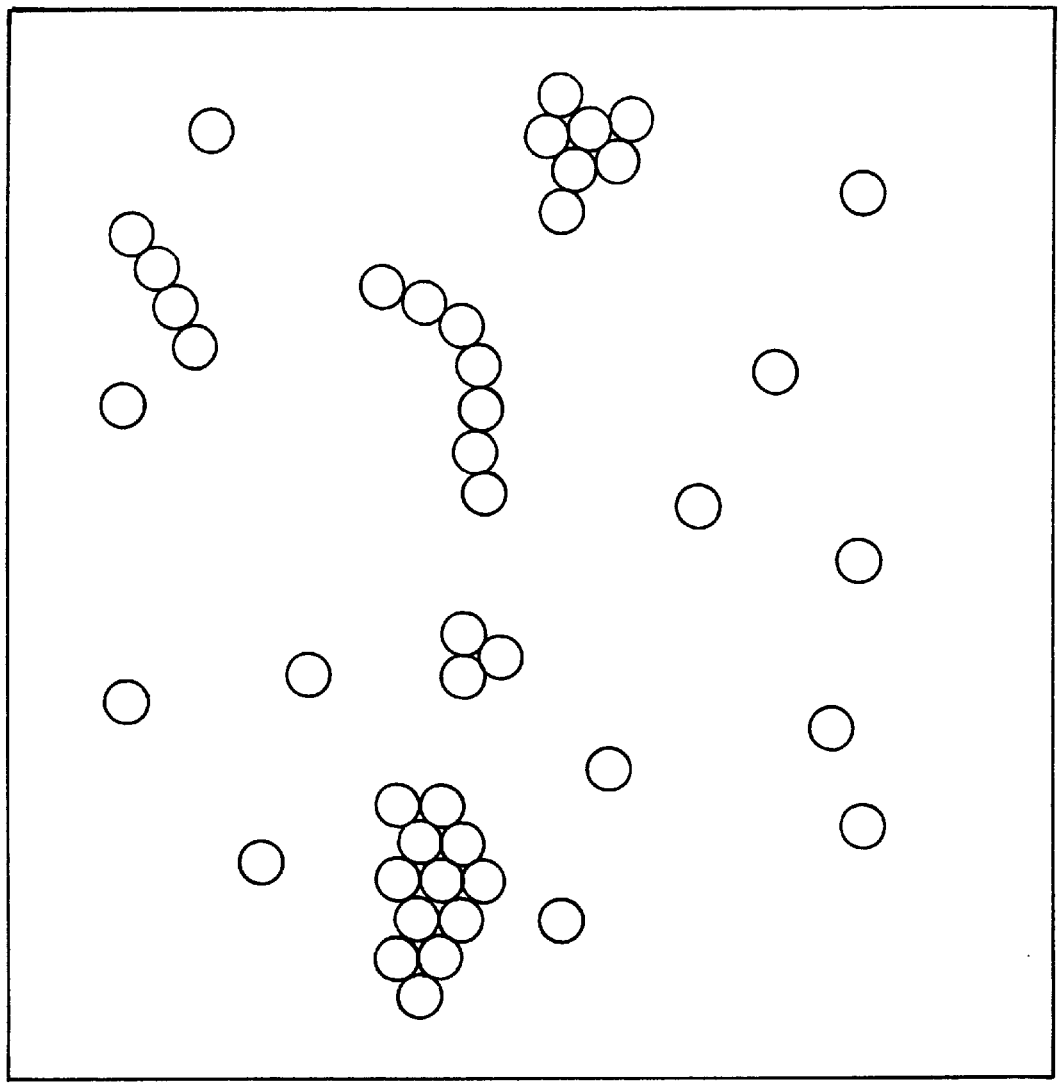
FIG. 1 is a representation of paramagnetic beads in a uniform magnetic field, disposed on a substrate.
Figure 2:
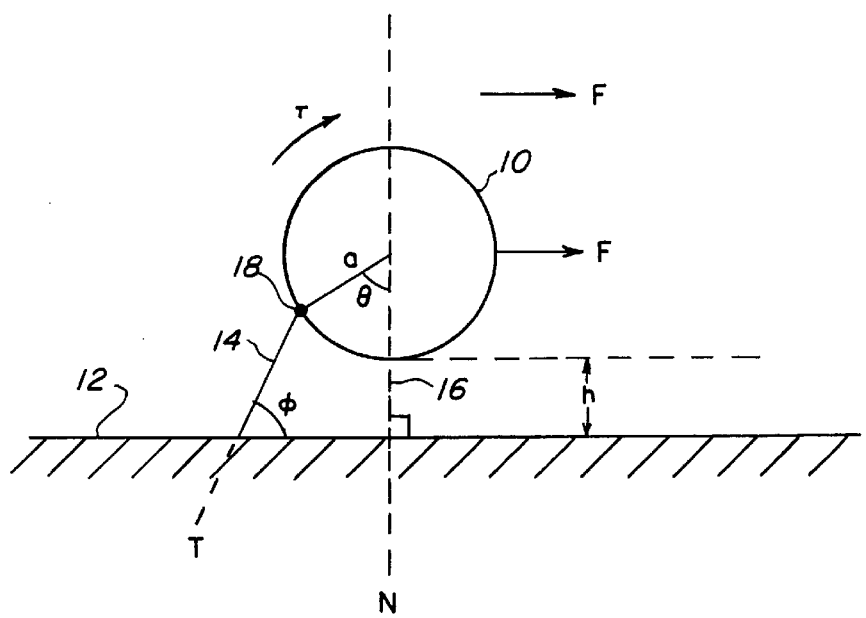
FIG. 2 is a schematic of a bead attached to a substrate, illustrating the significant forces acting on the bead (used with permission from K-C Chang et al., *Langmuir* 12, 2271–2282, Copyright (1996) American Chemical Society).

One aspect of this is to have the force operate on the beads at a uniform angle, preferably 90°, relative to the substrate, across the sample area. A force applied to the bead 90° relative to the substrate is directly transduced to the point of contact of the bead with the surface. The effect of tangential forces can be determined by executing a force balance on a spherical particle attached to a surface at a single point (FIG. 2). K.-C. Chang et al., in "Influence of Direction and Type of Applied Force on the Detachment of Macromolecularly-Bound Particles from Surfaces", *Langmuir* 12(9) 2271–82 (1996), have analyzed the effect of tangential force on such a system. The tensile force T applied to a specific molecular interaction by a tangential force Ft is the component of force oriented in the direction of the specific molecular interaction $$Ft = T \cos \phi.$$

Figure 3:
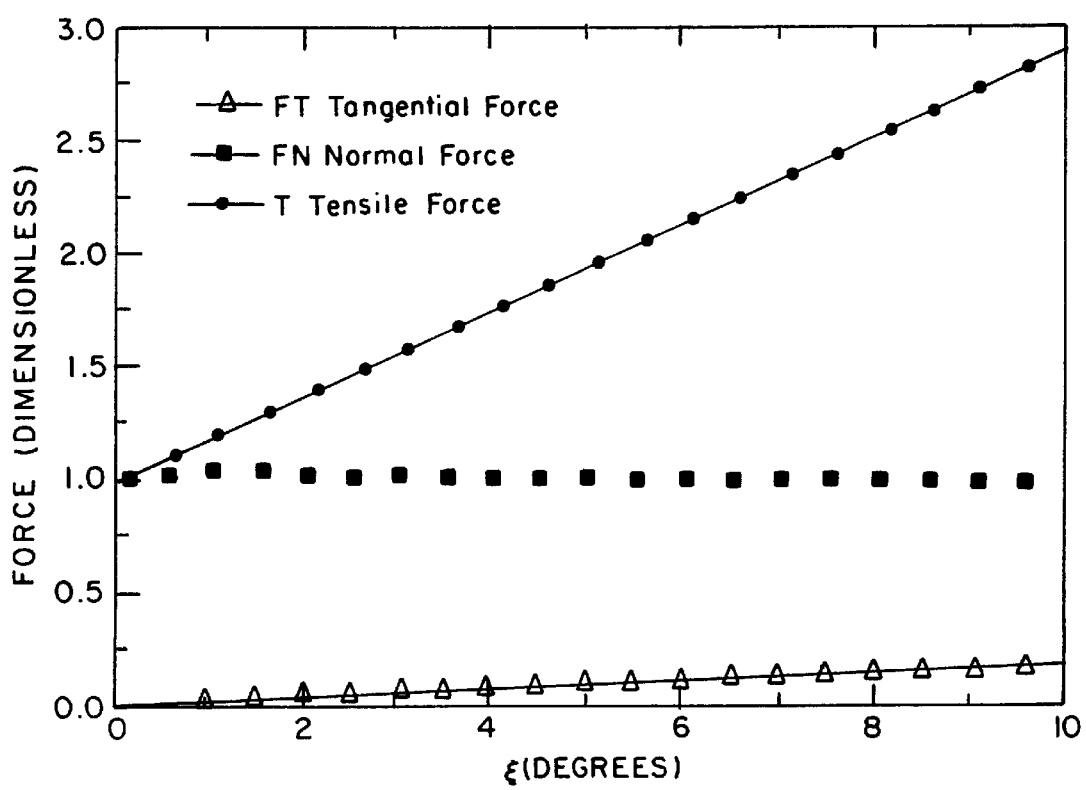
FIG. 3 plots the angular dependence of tensile and normal forces on beads.

The tilt of the bead, $\phi$, is determined by the geometry of the system $$Ft = T\sqrt{\frac{2(L-h)}{a}},$$

where L is the length of the specific molecular interaction complex, h is the surface roughness of the bead and a is bead radius. Given the properties of a typical bead (a=1,250 nm and h=5 nm) and complex (L=10 nm) the effect of tangential force on the specific molecular interaction is amplified by approximately a factor of 11. The angular dependence of the tensile and normal forces, FIG. 3, show the dramatic effect of small variations in the orientation of the force. Accordingly, a preferred feature of the invention is to apply the external force to the beads normally and without torque.

Figure 4:
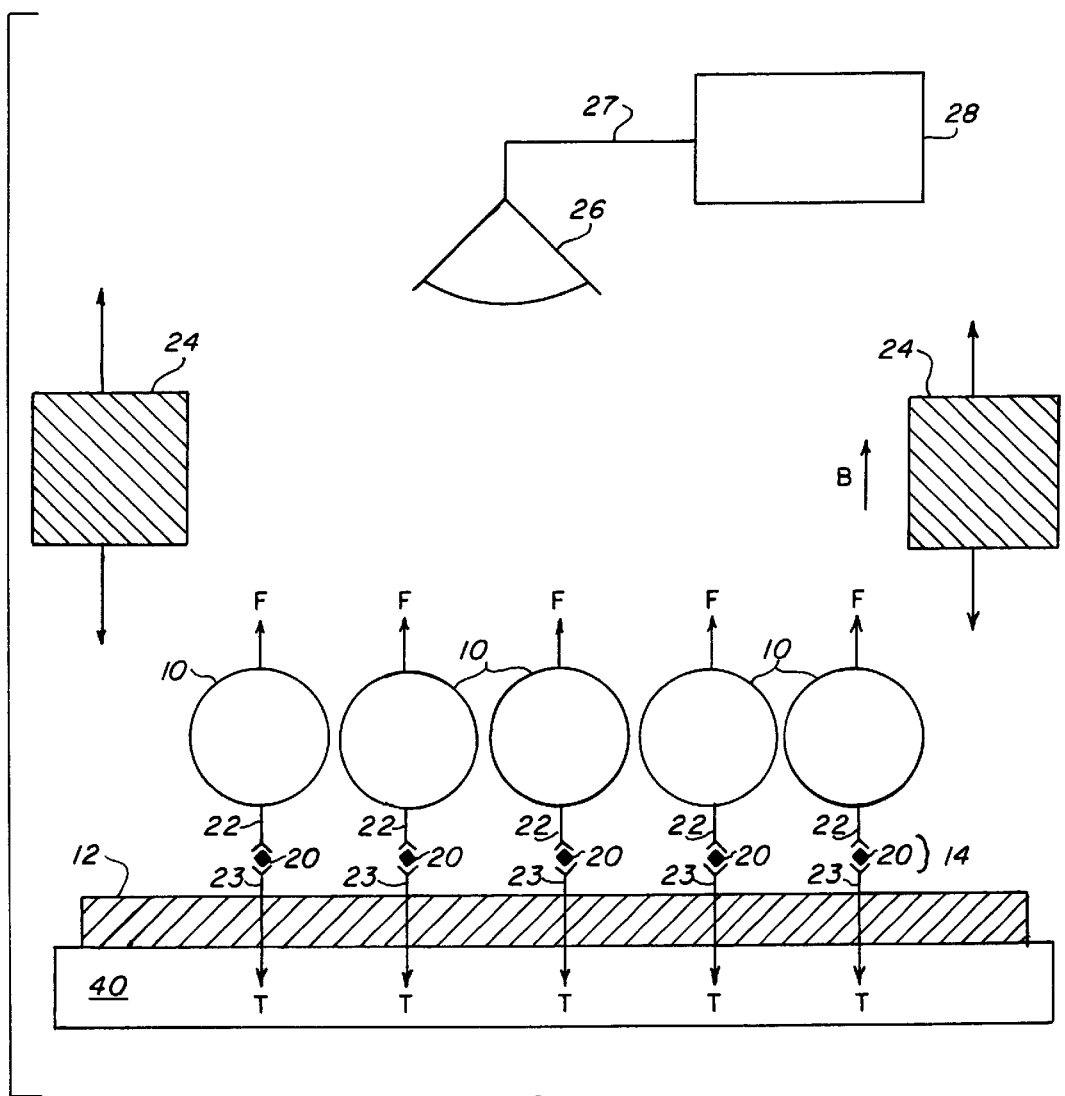
FIG. 4 is a schematic of an apparatus according to the invention, using a plurality of beads, in sandwich assay configuration.

Referring to FIG. 4, depicting a sandwich assay configuration for the present invention, one or more beads 10 and a substrate 12 are disposed in solution. The bead 10 is modified with molecules which are referred to herein as bead modifiers 22, and the substrate 12 is modified with molecules that are referred to herein as substrate modifiers 23. Both of these types of modifiers will be selected from those molecules that are capable of recognizing and selectively binding other molecules, including antibodies, haptens, polynucleic acids, polypeptides, glycolipids, hormones, polymers, metal ions, and certain low molecular weight organic species.

The mechanism for applying a variable, normal field to the bead 10 is shown here as a movable annular magnet 24. The annular magnet produces a uniform $\vec{B}$ field which is oriented along its axis across millimeter size areas. It has been discovered that a millimeter scale NdFeB magnet can apply a uniform field over sample areas consistent with imaging by optical microscopy, if the magnet is carefully centered. This normal B field acts upon the bead 10 to create a normal force (F) on bead 10, which in turn puts tension on the bond 14 between the bead 10 and the substrate 12. Since covalent bonds are typically much stronger than specific molecular interactions (such as antibody-hapten interactions), the strength of the linkage 14 between the bead 10 and the substrate 12 is limited by the strength of this specific molecular interaction.

In addition to annular magnets, other magnetic geometries may be used, such as discs, bars, or other flat shapes, so long as the B field has the desired properties in the area under observation. High permeability focusing cones positioned between the magnet and the substrate may be used to shape the field so that the field has a higher gradient. Since the force on a paramagnetic bead is related to the field gradient (see below), the use of these cones will tend to increase the forces acting on the beads.

As the field intensity is varied, eventually a point is reached where the bead separates from the substrate, indicating that the force from the field has exceeded the strength of nonspecific or specific molecular interaction. By observing when beads separate from the substrate, one can observe when this point is reached. It should be noted that the inventor has observed this separation point will depend not only on the force applied to the linkage between the bead and the substrate, but also on the observation time and the system temperature, as will be discussed below.

A preferred embodiment of the invention further comprises a microscope, typically an optical microscope 26, for imaging beads bound to the substrate, and separated from the substrate. Preferably, the microscope 26 is connected through connecting electronics (often including a video camera) 27 to a computer 28 or to a video recorder for analyzing images from the microscope. The advantage of the annular magnet 24 is that it does not interfere with transmitted light in an optical microscope. However, reflected light microscopy makes it possible to use solid magnet geometries.

Preferably, a population of modified beads are used in the present invention, rather than a single modified bead. The large number of beads simultaneously sample the entire sensor area overcoming diffusion limitations to the sensitivity of the detector.

For this preferred embodiment of the invention, it will be important to have the capacity to identify single beads (as distinguished from aggregates), to count the beads quickly and reliably, and to determine their relative position on the substrate. This positional information is advantageous for several reasons. For example, in some applications it may be advantageous to pattern the substrate by attaching different types of substrate modifiers on different regions of the substrate. It will be advantageous in such applications to identify where on a substrate a given bead is bound. Accordingly, the imaging system for the present invention, including the microscope 26, computer 28, and connecting electronics 27, should have the capacity to count beads that have separated from the substrate (or, alternatively, count beads that have not separated from the substrate). Typically, this will mean capturing a digital image from the microscope (either directly using a frame grabber or indirectly using a video recorder) and analyzing it using image analysis algorithms on the computer 28.

Additionally, it is preferred to provide a translation stage 40 for mounting the substrate, to permit the microscope to image various areas on the substrate with repeatability. It is further preferred to use a microscope that has fluorescence detection capability. When a translation stage 40, a microscope with fluorescence detection capability, and substrate with different types of substrate modifiers on different regions of the substrate, the apparatus may be used to detect a plurality of different target molecules with great facility (multiplexing).

Additionally, the imaging system for the present invention preferably has the capacity to discriminate between single beads on the substrate and clusters of two or more beads on the substrate, based on their size. It has been discovered that non-uniform surface chemistries and magnetic fields of the structures taught by Rohr produce the following non-ideal behavior.

Brownian motion causes the beads to move on the surface. This motion leads a significant fraction of the beads to form dimers and aggregates, if the beads are "sticky" (i.e., tend to stay together once they are brought together). Multi-body interactions in these aggregates lead to enhanced magnetization of the clusters when the $\vec{B}$ field is applied, and greatly accelerates their displacement. Image analysis allows one to identify the level of aggregation and correct for its effects. It should be noted that the fraction of beads as monomers and aggregates is strongly related to the amount of analyte on the surface and the nonspecific adhesive properties of the surfaces; therefore, aggregation can also be used to independently determine analyte concentration and surface properties.

Furthermore, under all but the most ideal circumstances a fraction (2–20%) of the beads adhere to the surface nonspecifically, even under high forces (>2 pN). It has been observed that these beads capture other beads that move laterally in the solution, and thus form string shaped aggregates. Image analysis makes it possible to identify these aggregates and discard them from consideration. Detection techniques that measure integrated signals can not distinguish these beads from specifically bound beads.

Nonspecific adhesion between beads, and between beads and the substrate, appears to increase when the beads are loaded with proteins, which suggests protein—protein interactions are the primary source for this adhesion.

It has been discovered that a commercially available microscope (Axiovert 100 microscope with a 63× Acroplan objective, Carl Zeiss, One Zeiss Dr., Thornwood, N.Y. 10594), electronics (VE-1000 CCD72 black/white video system from DAGE-MTI, Michigan City, Ind.; DT 3152 Fidelity PCI frame grabber, Data Translation, 100 Locke Dr, Marlboro, Mass. 01752-1192), image analysis software (Image-Pro Version 2.0, Media Cybernetics, 8484 Georgia Ave., Silver Spring, Md. 20910), and computer (Pentium 66 MHz Computer with 1 GB hard drive) will reliably identify superparamagnetic 2.6 micron diameter beads and clusters thereof. Once clusters have been identified, they can be ignored, i.e. discounted from further analysis. Thus, when the position of the beads is monitored (i.e., monitored for whether the beads are bound or unbound to the substrate), only single beads will be analyzed, dramatically improving the accuracy of the detector.

It has further been discovered that beads imaged through such a microscope may be monitored for movement, and that unbound beads will move over a time scale of a few seconds, permitting these beads to be identified as unbound, and likewise discounted from further analysis.

The magnitude of the adhesive force between the bead and surface is determined by several factors, i.e., the magnitude of the nonspecific forces, the number of specific molecular interactions linking the bead to the surface and the manner in which these interactions are stressed.

Surface modification chemistries (described below) have been developed that consistently produce very low nonspecific adhesive forces in a majority of beads. Typically, 80–98% of the beads can be removed from a surface at force equivalent to their buoyant weight, i.e., $\approx$40 femtoNewtons (fN) in the case of Dynal's M280 beads. The number of specific molecular interactions linking a bead to the surface will depend on the density and flexibility of ligands and receptors on the bead and surface.

Using Hertzian contact mechanics we can estimate the area of contact of a 2.6 micron sphere under a 40 pN load assuming the elastic modulus of the materials is $10^{10}$ Pa (K. L. Johnson, "Contact Mechanics," 1985 Cambridge University Press, New York, N.Y.). The calculated contact radius is 0.15 nm which is significantly smaller than the size of a typical ligand or receptor which makes a single intermolecular interaction most probable. However, the fact that the ligands and receptors are bound to the surfaces through polymeric linkers could enable multiple intermolecular interactions to take place.

In fact, it has been discovered that unless steps are taken to mitigate, typically there will be more than one specific binding linkage between a bead and the substrate, despite the small contact area between a flat surface and, e.g., a 2.6 $\mu$m diameter sphere. This discovery has been predicated on the observation that typical antibody-functionalized spheres may adhere to an antigen-coated surface with a force much greater than 200 pN. One would expect these beads to adhere with forces less than about 200 pN if they were attached through a single antibody-antigen linkage, given that the biotin-streptavidin interaction (one of the strongest in nature) only has a binding strength of about 250 pN.

To mitigate these effects, skilled practitioners will minimize the roughness of the interacting surfaces. In particular, it is preferred to keep the peak-to-valley roughness of the substrate $\leq$ca. 30 nm. In addition to the roughness of the interacting surfaces, other factors that skilled practitioners may identify as influencing the number of molecular interactions between a bead and a substrate include (a) the surface density of antibodies and antigens on these beads and substrates, (b) the mechanical properties of the beads and substrates, and (c) the steric mobility (flexibility) of the polymer used to attach the antibodies and antigens to the surface.

It has been discovered that a linkage between a bead and a substrate that comprises a specific binding interaction, such as an antibody/hapten interaction, has a lifetime that can be described by a Boltzmann probability curve (G. U Lee, et al, Langmuir 1994, 10 pp. 354–357). It has been discovered that this lifetime may be described by the equation $$\tau = \tau_0 e^{-(E - F \times d)/kT}$$

where $\tau$=the lifetime of a bond, $\tau_0$=a constant associated with the bond, F=applied force, E=the bond energy, d=distance associated with ligand receptor interaction and kT=thermal energy. The coupling of interaction force and the length of time the bond is loaded has important implications for the behavior of the beads under an applied force. For example, the bond strength of the intermolecular interaction will appear stronger over shorter time frames. If the rate of loading is too slow it may not be possible to distinguish a specific rupture force from a nonspecific force.

In addition to sandwich assay embodiments, the invention may be practiced in the other immunoassay configurations, e.g., competitive assay and displacement assay embodiments.

In a competitive assay according to the invention, the substrate is modified with the target molecule, or a portion thereof, and the beads are modified with a molecule capable of specifically binding to the target molecule. Free target molecules will compete with the substrate bound target molecules for binding sites on the beads. If a bead is completely complexed with the analyte target molecules, such that there are no accessible binding sites available for binding to the substrate, the bead will not specifically bind to the substrate. In this embodiment of the invention, it may be preferable to limit the number of binding sites on the beads. More preferably, the beads will have only a small number of binding sites (e.g., $\leq$10). In this way, a small number of free target molecules that interacts with a bead will be sufficient to prevent that bead from complexing with the substrate.

In a displacement assay according to the invention, the substrate is modified with a molecule capable of specifically binding to the target molecule, and the beads are modified with the target molecule, or a portion thereof. If the beads are complexed with the substrate, and target molecules are introduced into the solution, a target molecule will have a certain probability of displacing a bound bead on the substrate, freeing that bead to separate from the substrate in the applied field. Alternatively, the analyte may be premixed with the modified beads, and the beads and analyte may be added to the substrate together.

Typically, it will be advantageous to limit nonspecific adsorption by coating the substrate with an agent that minimizes nonspecific adhesion. It has been found that commonly used blocking agents, such as bovine serum albumin (BSA) are less useful for the present invention, because the physically adsorbed BSA molecules are not covalently linked to the surface, may be displaced by molecules with higher binding affinities for the substrate and may act as a bridging agent under some conditions. To get the advantages of limited nonspecific adsorption, another method should be used.

It has been discovered that certain chemisorbed polymers, such as polyethylene glycol (PEG), will reduce nonspecific adhesive particle-substrate forces by producing strong repulsive forces. The origin of the repulsive force is still an issue of some scientific debate, but is believed to originate from the unfavorable entropic energy that is required to compress the chemisorbed polymer (Intermolecular and Surface Forces, J. Israelachvili, Academic Press, San Diego, 1992).

PEG is a nonionic, water soluble polymer that may be grafted to surfaces through formation of a block copolymer or chemical conjugation. The inventor has used a heterobifunctional PEG, i.e. a PEG with two different chemical groups on its ends, with molecular weight of about 3400, to covalently graft a binder to the active surface for the assay. PEG have been grafted to both glass and plastic surfaces using polyethyleneimine (PEI). PEI is a water soluble commercially available polymer with a high density of primary and secondary amines. It is easily modified with a high degree of specificity and efficiency using cross-linkers such as N-hydroxy succinimide. This chemistry is based on work done to modify surfaces to minimize protein adsorption (Brink, et al., Solid surface coated with a hydrophilic biopolymer-repellent outer layer and method for making such a surface, U.S. Pat. No. 5,240,994).

Protocol for PEG surface modification:

1. The surface was first cleaned using an appropriate technique known to those skilled in the art. For example, plastic surfaces that were fairly clean were sonicated in a 70:30 mixture of ethanol:water.

2. Polymer surfaces were oxidized using, 4% $KMNO_4$ in concentrated sulfuric acid.

3. The surfaces were exposed to a 3% PEI (Polymm SNA, BASF, Mount Olive, N.J.) solution in 50 millimolar (mM) carbonate buffer pH 8.2 for two hours and washed with water at least 3 times.

4. 10 mg/ml solutions of NHS-PEG-Biotin, heterobifunctional PEG, or SPA-PEG (Shearwater Polymers, 2304 Spring Branch Road, Huntsville, Ala.) in carbonate buffer, pH 8.2, were incubated with the surfaces for at least 12 hours.

5. Surfaces were washed with phosphate buffer saline (PBS, 100 mM sodium chloride, 50 mM phosphate) and the assay was run.

In addition to use as an assay, the apparatus of the invention may be used to characterize the strength of specific binding interactions, i.e., determining the nature of the interaction between a target species and a species that undergoes a specific binding interaction with that target species. For instance, the substrate may be modified with substrate modifiers selected from the group of antibodies, polynucleic acids, polypeptides, glycolipids, hormones, polymers, metal ions, chelating agents, and hormones, and one or more magnetically active beads may be modified by attaching bead modifiers selected from the group of antibodies, polynucleic acids, polypeptides, glycolipids, hormones, polymers, metal ions, chelating agents, and hormones, where these bead modifiers have a binding affinity for the substrate modifiers in the presence of the target species, and a measurably different binding affinity for the substrate modifiers in the absence of the target species. The beads or surfaces are then disposed in a solution containing the target molecule.

The beads are then permitted to interact with the substrate. These interactions typically include both specific and non-specific interactions. A magnetic field is applied to the beads, preferably normally with respect to the substrate, for pulling the beads away from the substrate. This field typically starts at a low strength, and is gradually increased in strength, until the beads, or a predetermined fraction of the beads, separate from the substrate.

Figure 5:
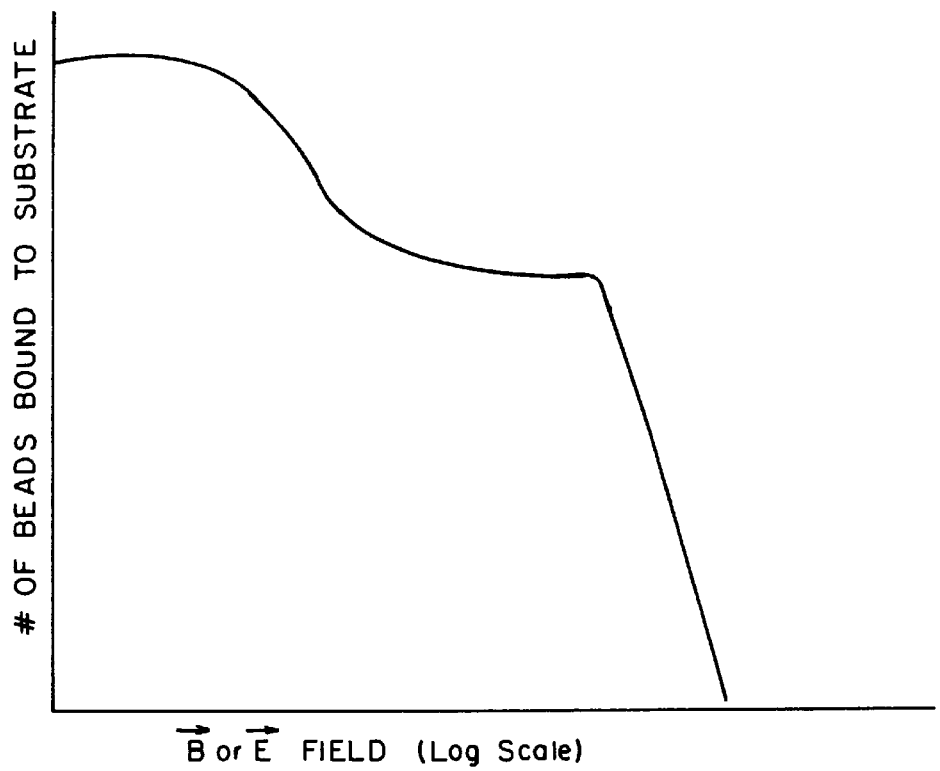
FIG. 5 is a hypothetical force vs. bead release curve.

FIG. 5 is a hypothetical force vs. bead release curve for an optimal time and temperature. One sees from FIG. 5 that the separation of the beads from the substrate will occur in roughly two stages: a first stage at lower field, corresponding to the removal of non-specifically bound beads, and a second stage, corresponding to the removal of specifically bound beads. The second stage will occur at higher field strengths than the first stage and will be highly dependent on the rate at which the force is applied to the beads. By varying the rate at which the forces is applied to the beads it is possible to measure the three critical parameters necessary to characterize the specific molecular interaction $\tau_0$, E and d. Of course, if the bead-substrate interaction is more complex (i.e., more than one type of interaction) the separation curve may show more than two stages.

Several different types of beads are suitable for use in the present invention.

Paramagnetic materials have a net magnetization $\mu$ only in the presence of an applied external field $\vec{B}$. Nonporous paramagnetic beads (usually made from an impregnated polymer) are used for magnetic separation in molecular biology because of their relatively low density and lack of residual magnetism. They may also have surface functional groups (such as amine or carboxyl) that may be used to covalently immobilize receptors (e.g., streptavidin, antibodies, or DNA). See Technical Handbook of the Dynal Co, 5 Delaware Dr., Lake Success, N.Y. 11042; Lund, V., Schmid, R., Richwood, D., Hornes, E. (1988) 16(22) 10861–10880. Magnetic beads can be used for separation of analytes in complex mixtures by immobilization of the analyte on the bead followed by separation of the beads in a magnetic field. Several patents and patent applications have described the use of magnetic beads for detection applications.

The force acting on a small paramagnetic specimen in a nonuniform magnetic field is given by $$F = \mu \frac{\partial B}{\partial x}$$

where $\mu$ (=$\chi B$) is the magnetization (i.e., magnetic dipole moment) of the specimen, and $$\frac{\partial B}{\partial x}$$

is the magnetic field gradient.

Paramagnetic beads are desired for this embodiment of the invention, because the beads will have a magnetization only when an external field is applied. Thus, the beads will not tend to clump together, which would potentially interfere with their interaction with the target species. However, ferromagnetic beads may be substituted, especially if certain precautions are taken.

Ferromagnetic materials have a net magnetization $\mu$ after being magnetized in an applied magnetic field. This magnetization is permanent until a coercive field is applied, or until the material is raised above its Curie temperature. Nonporous ferromagnetic beads are also available. Like paramagnetic beads, they may also have surface functional groups that may be used to covalently immobilize receptors. See Wang, N., Butler, J. P., Ingber, D. E. (1993) Science 260, 1124–1127.

If ferromagnetic beads are used, however, they generally should either (1) be kept above their curie temperature until, in situ, one is ready to perform an analysis, or (2) not be magnetized in a magnetizing field until, in situ, one is ready to perform an analysis.

Commercially available beads with diameters between about 0.2 $\mu$m and about 200 $\mu$m have surface areas that are large enough to apply high quality uniform coatings, in a manner consistent with the objects of the invention. Such beads typically will experience forces of magnitudes that are likewise consistent with the objects of the invention under reasonable applied fields. Fortunately, such beads are also viewable with the preferred optical microscopes of the invention. This synergism between the beads, the fields, and the preferred optical microscope viewing mechanism is particularly advantageous.

Physical properties of two exemplary types of paramagnetic beads from Dynal are listed below. These beads have a large, uniform size that is well suited to counting. Moreover, the total force that can be transduced to them is large. Currently, however, at least about a dozen companies sell superparamagnetic beads suitable for biological separation, including Bang and Biomag (both of whom make smaller beads with higher magnetizations).

Properties of two types of Dynal beads:

|  | M280 ® | M450 ® |
|---|---|---|
| Average diameter ($\mu$m): | 2.8 ± 0.2 | 4.5 ± 0.5 |
| Density (g/cm$^3$): | 1.34 | 1.55 |
| Mass/bead (pg): | 17.2 | 71.4 |
| Magnetization[1] (emu/cm$^3$): | 14 H/(257 + H) + 7 · 10$^{-5}$ H | 7.8 H/(238 + H) + 6.9 · 10$^{-5}$ H |

[1] Magnetization is based on measurements made at the Naval Research Laboratory using a SQUID magnetometer.

Figure 6:
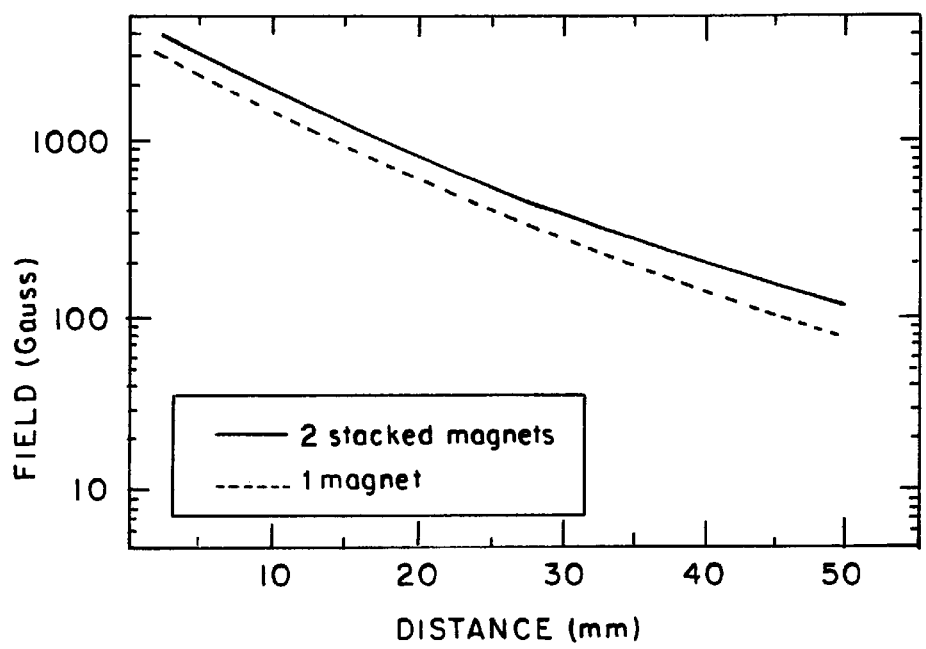
FIG. 6 plots the magnetic field generated by one and two NdFeB magnets versus distance.

FIG. 6 plots the magnetic field generated by one and two NdFeB magnets versus distance. The magnets were 1"×1"× 0.5" blocks of sintered NdFeB magnetized along the short axis (Magnet Sales & Mfg. Co., 11248 Playa Ct., Culver City, Calif.). Note that the gradients for one and two magnets are virtually identical, and that two magnets have a slightly higher field than one magnet.

Figure 7:
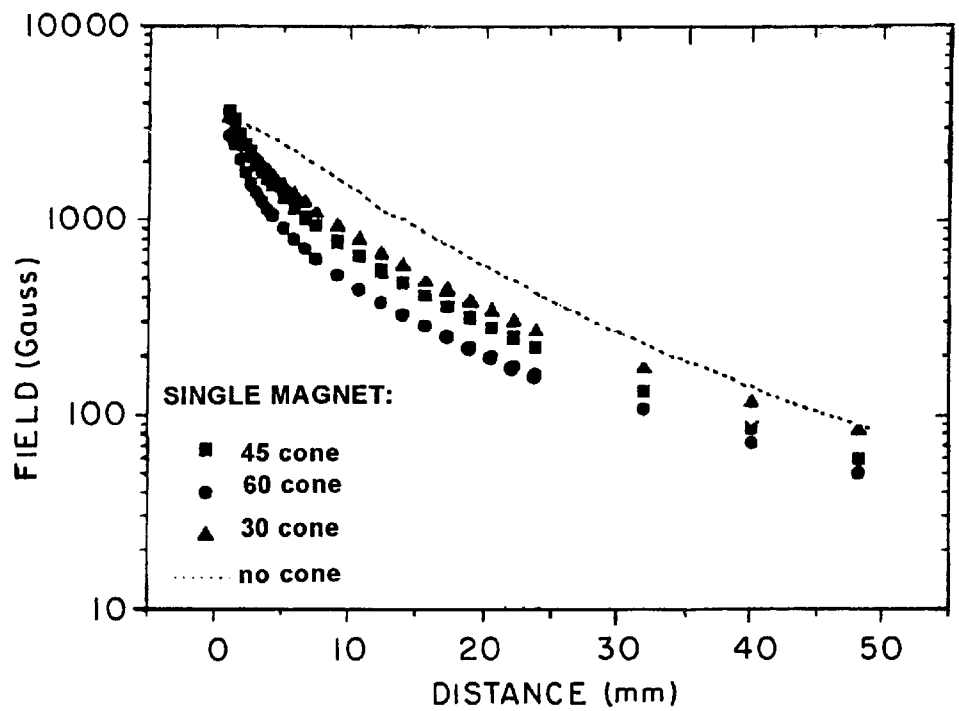
FIG. 7 plots the magnetic field generated by an NdFeB magnet with various field focusing cones versus distance.

FIG. 7 plots the magnetic field generated by an NdFeB magnet with various field focusing cones versus distance. Note that at short distances, especially below 10 mm, the gradients for magnets with field focusing cones are significantly higher than the gradient for a magnet without a field focusing cone. It has been observed that sharper cones produce larger field gradients, but will also reduce the area where there is essentially no lateral component to the field. Thus, for a given magnification, there will be a maximum cone angle that can be used without observing significant lateral forces. However, larger fields of view are desired to provide higher bead counts.

For these beads, the force in a nonuniform field then becomes $$F = \mu \frac{\partial B}{\partial x} = 0.524 \, Md^3 \frac{\partial B}{\partial x}$$

where M is the volume magnetization listed as a function of H in the preceding table, and d is the particle diameter. Skilled practitioners will seek to optimize the force acting on the beads used in the sensors of the invention by optimizing the magnetic field producing system, and the approach system for bringing the substrate into proximity with the magnetic field producing system.

Having described the invention, the following examples are given to illustrate specific applications of the invention, including the best mode now known to perform the invention. These specific examples are not intended to limit the scope of the invention described in this application.

EXAMPLES

Example 1

Detection of Biotin in a Competitive Assay

The principle of FDA was first demonstrated with the model ligand and receptor system streptavidin and biotin. Streptavidin is a protein with four receptor sites for biotin that are located in two sets on opposing sides of the molecule. The biotin-streptavidin interaction was chosen as it is among the strongest interactions that occur in nature, i.e., k=10$^{15}$ M$^{-1}$ (M. B. Savage, "Avidin-Biotin Chemistry: A Handbook" Pierce Chemical Co, 1992).

Biotin was detected in the form of biotinylated bovine serum albumin (BBSA), i.e., bovine serum albumin to which ~8 biotin molecules have been covalently attached through the primary amines. BBSA was used rather than biotin as it minimizes the nonspecific adhesion of the beads with the surface. Varying concentrations of BBSA were incubated with separate aliquots of streptavidin-functionalized superparamagnetic beads (Dynal, Lake Success, N.Y.), the beads were incubated with separate biotin-PEG microscope slides and a force was applied to the beads while observing their relative position in a video enhanced optical microscope (described above).

Figure 8:
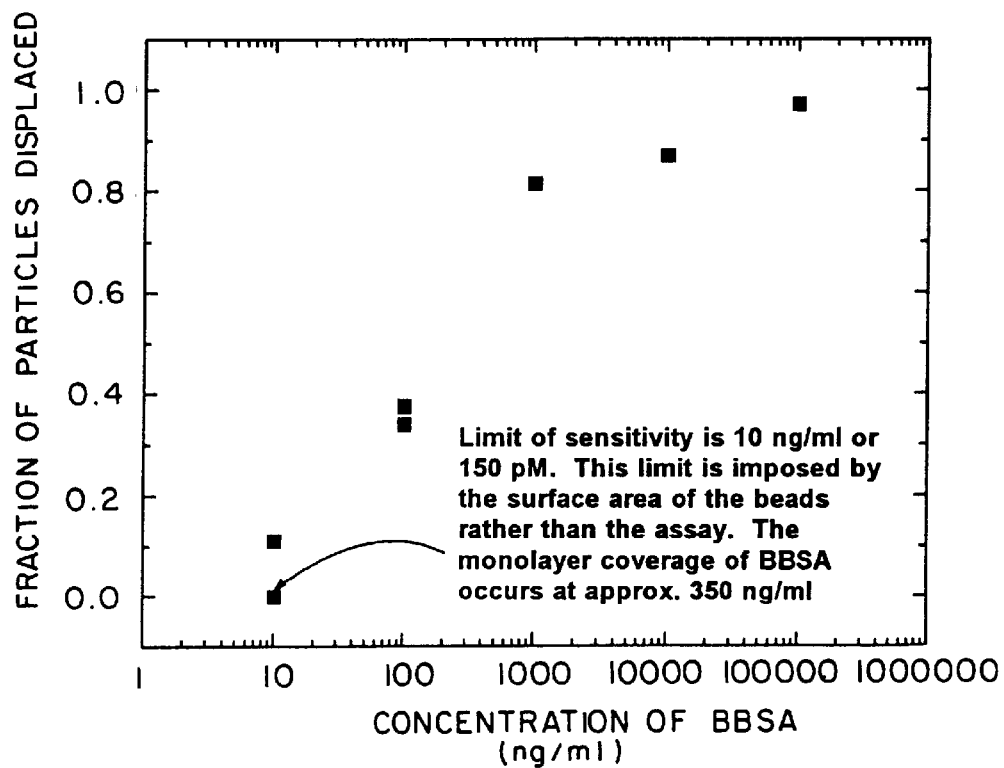
FIG. 8 plots the results of a competitive biotin assay.

At a critical force, the force pulling the beads away from the surface overcomes nonspecific adhesion and gravitational forces, and beads that were not specifically adsorbed were lifted off the surface. The number of beads specifically adhering to the surface was measured with the video microscope and the results of the assay are reported in terms of fraction of particles bound in FIG. 8.

The limit of sensitivity of the assay is 10 ng/ml of BBSA. This sensitivity limit is imposed by the large surface area and streptavidin activity of the commercial beads. Total theoretical coverage of the beads is achieved at 350 ng/ml of BBSA.

The detailed procedure used for the biotin assay is set forth below.

1. Preparation of beads: 0.15 ml of streptavidin functionalized beads (M-280, Dynal, Lake Success, N.Y.) was washed three times with PBS, 0.1% bovine serum albumin (BSA) (together PBS-BSA), and incubated overnight in PBS-BSA. The beads were separated from the PBS-BSA solution and re-suspended in 0.4 ml of PBS. 0.05 ml of solution (0.1875 mg of beads) was incubated in 0.4 ml of various concentration of BBSA in PBS for 2 hours.

2. Preparation of assay cells: Glass microscope slides were functionalized with PEG-biotin using a procedure similar to that described above, but a silane was used to functionalize the glass with primary amines rather than PEI (silanization is technique known to those skilled in the art and is described in detail in L. A. Chrisey, et al, "Covalent Attachment of Synthetic DNA to Self-Assembled Monolayer Films", Nucleic Acids Research 24, 1996, 3031–3039). A plastic ring was then glued to the glass slide with optical epoxy (Norland Products, Inc., New Brunswick, N.J.) and cured with UV light. The surface was blocked with 0.2 ml of PBS-BSA for at least 1 hour and rinsed with PBS.

3. Assay: 0.15 ml of the beads were added to the cells and incubated for 30 minutes. The cell was placed on the microscope and the number of beads in an area were counted using the CCD camera, digital frame grabber, and software described above. The number of beads bound to the surface were determined by lowering a ring-shaped magnet to a predetermined height above the cell (as described above), and counting the number of beads. Alternatively, the force and/or time required to displace the beads can be determined by approaching the magnet to the surface while acquiring images.

Example 2

Direct Detection of Ovalbumin Using a Sandwich Assay

FDA has been used to detect ovalbumin, a model protein analyte. This demonstrates that this assay can be used with molecular recognition interactions that are weaker than streptavidin-biotin, i.e., most antibody-antigen interactions. The sensitivity of the assay is currently 100 pg/ml of ovalbumin which is 10 times better than the standard enzyme-linked immuno sorbent assay (ELISA).

Figure 9:
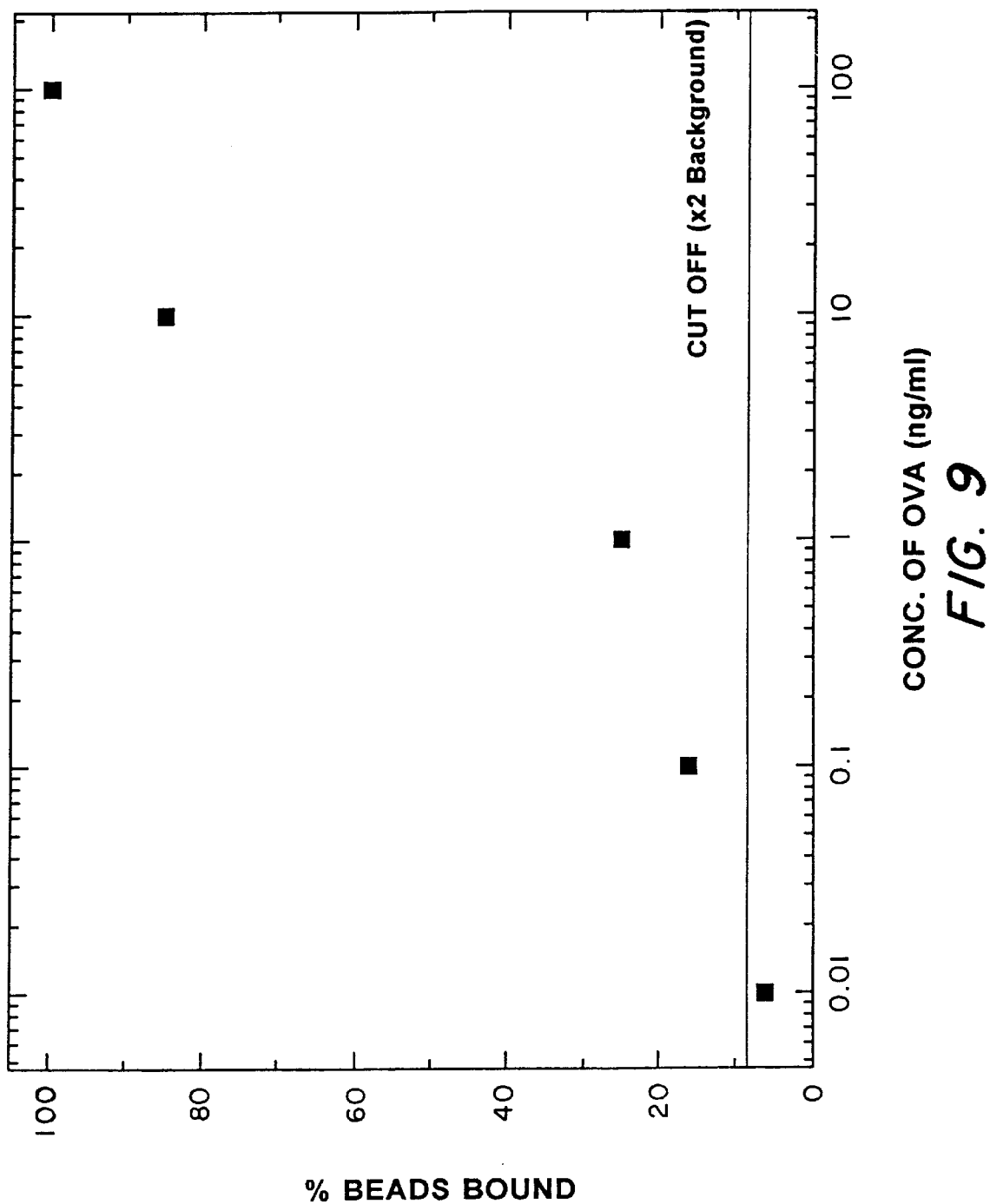
FIG. 9 plots the results of a direct assay For ovalbumin.

In this assay ovalbumin was bound between two IgG antibodies that have been raised against ovalbumin in goats (lot no. 210497-02, NMRI) and rabbits (lot no. 210497-01, NMRI). These antibodies bind non-overlapping epitopes (regions of the protein) and if used together bind ovalbumin in a sandwich conformation. The goat IgG was attached to a surface by first conjugating the antibody to streptavidin and then immobilizing on a PEG-biotin surface (chemistry described above). The rabbit antibody was covalently conjugated to tosyl functionalized super-paramagnetic beads. Like the biotin assay described in Example 1, a magnetic force was used to distinguish between specifically and nonspecifically adsorbed beads. The number of beads specifically adhering to the surface was measured with the video microscope, and the results of the assay are reported in terms of fraction of particles bound in FIG. 9.

The detailed procedures used for the direct detection of ovalbumin are set forth below.

1. Preparation of the surfaces: The assay was run in microtitration plates with polystyrene well, which are widely used for immunoassays. PEG-biotin functionalized microtiter plates were prepared using the PEI chemistry described above.

2. Preparation of the beads. A suspension of the tosyl activated M-280® Dynal beads were homogenized using a pipette and by vortexing for 1 min. 0.25 ml of the beads were removed from their storage medium, using magnetic separation. The beads were re-suspended in 0.5 ml of 0.1M phosphate buffer, pH 7.5. The beads were washed twice in phosphate buffer using magnetic separation. The antibody solution of 300 $\mu$g of antibody per 6×10$^8$ beads (5 $\mu$g per 10$^7$ beads) was dissolved in phosphate buffer. The antibody was added to the beads while vortexing the beads (keeping the vortex setting to 4) and continuing to vortex for 1 min. Mixing was done later using a rotary mixer at room temp. The tubes were incubated overnight at RT with mixing (16–24 hr.).

After incubation, the tubes were placed in the magnet for 1–4 min., and the supernatant was removed. The antibody-coated beads were washed four times: two rinses in PBS with 0.1% BSA buffer for 5 min., one rinse in 0.2 M Tris pH 8.5 with 0.1% BSA for 4 h at RT, and one rinse in PBS with BSA for 5 min. The beads were stored in PBS, 0.1% BSA.

The beads were washed twice with Triton X-100® to remove the physically adsorbed antibodies. The beads were washed for 5 min. with 0.01 M PBS with 1% BSA. The beads were washed for 5 min. with 1% Triton X-100 followed by two washes with 0.01 M phosphate buffer 1% BSA. The beads were re-suspended and stored in 1 ml 0.01 M PBS with 1% BSA.

3. Assay: The microtiter wells were washed with Q-water and PBS. The PBS was removed, and 200 $\mu$l 1% BSA in PBS was added to PEG-Biotin wells. The wells were incubated at room temperature for 1 hr. The beads were washed 3 times with PBST (PBS with 0.025% Tween20®). 100 $\mu$l of goat-antibody were added to ovalbumin-streptavidin at a concentration of 1 microgram/ml, and incubated for 1 hr. at room temperature. The beads were next washed three times with PBST. 100 $\mu$l of various dilutions of ovalbumin were added, and the beads were incubated for 1 hr. at room temperature. The beads were washed three times with PBST. 100 ml of PBS were added to the wells, and then 5 $\mu$l of the rabbit antibody were added to the beads (100,000 beads/well, diluted 1:5 in 1% PBS-BSA). The beads were incubated for 20 min. The beads were counted before and after exposure to the magnet.

Example 3

Indirect Detection of Ovalbumin Using a Sandwich Assay

This assay was similar to the direct assay used for ovalbumin in that rabbit and goat antibodies were used to sandwich the ovalbumin. The primary difference was that a goat antirabbit antibody is directly conjugated to the beads rather than an antibody against ovalbumin. The sandwich was assembled by adding ovalbumin to the goat antiovalbumin antibody functionalized surfaces, adding the rabbit antiovalbumin antibody to the surface and then adding the goat antirabbit antibody functionalized beads to the surface. The advantage of this assay is that its sensitivity is currently 10 pg/ml of ovalbumin which is 100 times better than ELISA.

The detailed procedures used for the indirect detection of ovalbumin are set forth below.

1. Preparation of the surfaces: PEG-biotin functionalized microtiter plates were prepared using the PEI chemistry described above.

2. Preparation of the beads. Same as described for the direct ovalbumin assay, except that goat antirabbit IgG is conjugated to the beads (antirabbit IgG (M+L) affinity purified, Vector Laboratories, Inc., 30 Ingold Rd, Burlingame, Calif. 94010).

3. Assay: The microtiter wells were washed once with Q-water and PBS. The PBS was removed and 200 $\mu$l 1% BSA in PBS was added to PEG-Biotin wells. The wells were incubates at room temperature for 1 hr, and washed three times with PBST. 100 $\mu$l of goat-antibody was added to ovalbumin-Streptavidin at a concentration of 1 microgram/ml, and incubated for 1 hr at room temperature, followed by three washings with PBST. 100 $\mu$l of various dilutions of ovalbumin and incubate for 1 hr at room temperature. The wells were again washed three times with PBST. 100 $\mu$l of various dilutions of rabbit antiovalbumin antibody were added and the wells were incubated for 1 hr at room temperature, followed by three washings with PBST. 100 ml of PBS was added to the wells, followed by 5 $\mu$l of goat antirabbit beads (100,000 beads/well, diluted 1:5 in PBS-BSA). The beads were well sheared by pipetting several times). The wells were incubated for 20 min. The beads were counted before and after exposure to the magnet.

Obviously, many modifications and variations of the present invention are possible in light of the above teachings. It is therefore to be understood that, within the scope of the appended claims, the invention may be practiced otherwise than as specifically described.

What is claimed is:

1. A sensor for a selected target species, comprising:
   a substrate which has been chemically modified by attachment of substrate modifiers capable of undergoing a selective binding interaction;
   one or more magnetically active beads which have been chemically modified by attachment of bead modifiers capable of undergoing a selective binding interaction, wherein said bead modifiers have a binding affinity for said substrate modifiers in the presence of said target species, and a measurably different binding affinity for said substrate modifiers in the absence of said target species;

an adjustable magnetic field source, adapted for producing an adjustable magnetic field for exerting a force on said beads; and an imaging system adapted for observing individually the magnetically active beads bound to said substrate, wherein the presence or absence of the target species is determined by the exerted force applied by the adjustable magnetic field required to separate an individual, magnetically active bead from the substrate.

2. The sensor of claim 1, wherein said substrate modifiers are selected from the group consisting of haptens, antibodies, nucleic acids, proteins, chelating agents, and selective binding polymers, and wherein said bead modifiers are selected from the group consisting of haptens, antibodies, nucleic acids, polypeptides, glycolipids, hormones, chelating agents, metal ions, and selective binding polymers.

3. The sensor of claim 2, wherein said substrate modifiers are attached to a cell.

4. The sensor of claim 1, wherein said imaging system comprises an optical microscope.

5. The sensor of claim 4, wherein said imaging system further comprises a digital image acquisition system.

6. The sensor of claim 5, wherein said imaging system further comprises a digital image processing system, for identifying images of beads.

7. The sensor of claim 1, wherein said one or more magnetically active beads comprise a plurality of beads.

8. The sensor of claim 7, further comprising a counting system adapted for counting beads.

9. The sensor of claim 7, wherein said plurality of beads has an average diameter between about 0.2 $\mu$m and about 200 $\mu$m.

10. The sensor of claim 1, wherein said adjustable magnetic field source is adapted for applying a field on said one or more magnetically active beads that is essentially normal to said substrate.

11. The sensor of claim 10, wherein said adjustable magnetic field source for applying an essentially normal field comprises a magnet adapted for producing an axially symmetric field gradient.

12. The sensor of claim 11, wherein said axially symmetric field gradient is a predetermined field gradient.

13. The sensor of claim 1, wherein said adjustable magnetic field source is adapted for applying a field on said one or more magnetically active beads that is essentially free of torque on said beads, and wherein said beads have a bead density below a predetermined bead density threshold that would produce an aggregation of said beads.

14. The sensor of claim 1, wherein said substrate has a first region with said attached substrate modifiers, and a second region adapted for resistance to nonspecific adsorption.

15. The sensor of claim 14, wherein said substrate has a water soluble polymer coating, said polymer coating modified in said first region by attachment of said substrate modifiers to said water soluble polymer, and wherein said water soluble polymer coating in said second region has an inherent resistance to nonspecific adsorption.

16. The sensor of claim 15, wherein said polymer is polyethylene glycol (PEG), adapted for attachment to said substrate and attachment of said substrate modifiers.

17. The sensor of claim 14, wherein said substrate has a polymer coating, said polymer coating modified in said first region by attachment of said substrate modifiers to said polymer, and wherein said polymer coating in said second region has attached moieties for reducing nonspecific adsorption.

18. The sensor of claim 16, wherein said PEG is coated onto said substrate by incubating a concentration of at least 10 mg/ml PEG.

19. The sensor of claim 16, wherein said PEG is coated onto said substrate by incubating a concentration of at least 2.9 mM PEG.

20. The sensor of claim 19, wherein said water soluble polymer is an functionalized PEG selected from the group consisting of monofunctional PEG and bifunctional PEG.

21. The sensor of claim 20, wherein said functionalized PEG is bifunctional PEG.

22. The sensor of claim 21, wherein said bifunctional PEG is heterobifunctional PEG.

23. The sensor of claim 1, wherein said sensor has two or more magnetically active beads which have been chemically modified by attachment of said bead modifiers.

* * * * *